United States Patent
Ruffing

(10) Patent No.: US 7,954,210 B2
(45) Date of Patent: Jun. 7, 2011

(54) HOSE CLAMP

(75) Inventor: Andreas Ruffing, Bexbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 952 days.

(21) Appl. No.: 11/883,370

(22) PCT Filed: Dec. 23, 2005

(86) PCT No.: PCT/EP2005/013969
§ 371 (c)(1),
(2), (4) Date: Jul. 31, 2007

(87) PCT Pub. No.: WO2006/081866
PCT Pub. Date: Aug. 10, 2006

(65) Prior Publication Data
US 2008/0141498 A1    Jun. 19, 2008

(30) Foreign Application Priority Data
Feb. 2, 2005    (DE) .......................... 10 2005 004 863

(51) Int. Cl.
*B65D 67/02* (2006.01)
*A61M 39/28* (2006.01)
(52) U.S. Cl. .............................. 24/489; 24/543; 604/250
(58) Field of Classification Search .................... 24/489, 24/543; 604/250; 251/10
See application file for complete search history.

(56) References Cited

U.S. PATENT DOCUMENTS

| 5,035,399 | A * | 7/1991 | Rantanen-Lee | 251/10 |
| 5,238,218 | A * | 8/1993 | Mackal | 251/10 |
| 6,161,812 | A * | 12/2000 | Guala et al. | 251/10 |
| 6,742,760 | B2 * | 6/2004 | Blickhan et al. | 251/11 |
| 2002/0169423 | A1 * | 11/2002 | Zoltan et al. | 604/250 |

FOREIGN PATENT DOCUMENTS

| DE | 90 11 416 U1 | 10/1990 |
| DE | 698 26 474 T2 | 2/2005 |
| EP | 0 948 971 A1 | 10/1999 |
| EP | 0 995 461 A1 | 4/2000 |
| WO | WO 2004/041343 A1 | 5/2004 |

* cited by examiner

*Primary Examiner* — Robert J Sandy
(74) *Attorney, Agent, or Firm* — Jacobson Holman PLLC

(57) ABSTRACT

A hose clamp, preferably for the closing of catheter extensions, has an integral plastic body extending in an elongate manner with two arms which are resiliently connected to one another at the ends and which each form a projection such that they are disposed opposite one another in the closed state of the hose clamp. The arms can be hooked with one another in the closed state with openings being provided at the front and rear ends thereof for the reception of a hose. The hose clamp generally has the shape of a cylinder with cut-off sides which taper conically at both sides toward the ends of the clamp, with the ends being adapted to the circular shape of a hose is received therein.

10 Claims, 2 Drawing Sheets

Section B-B

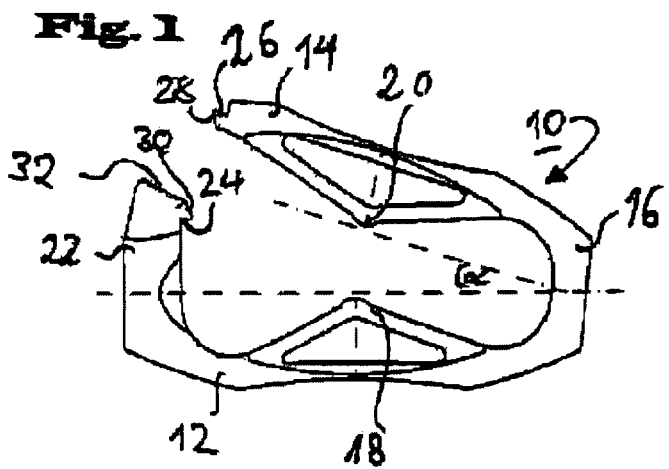
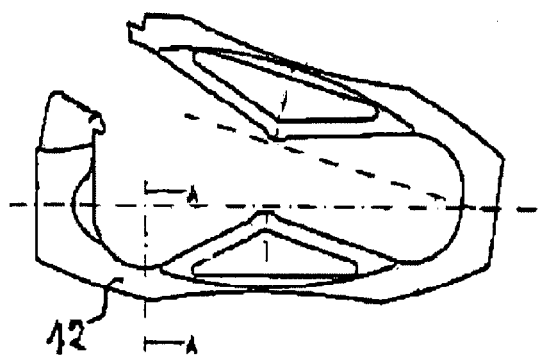
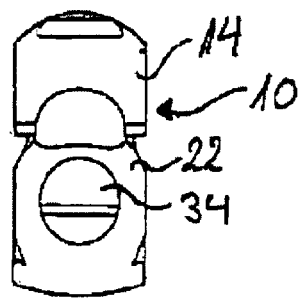

Section B-B

HOSE CLAMP

CROSS-REFERENCE TO RELATED APPLICATION

This is a national stage of PCT/EP2005/013969 filed 23 Dec. 2005 and published in German.

BACKGROUND OF THE INVENTION

1. Field of Invention

The invention relates to a hose clamp, preferably for the closing of catheter extensions.

2. Description of the Prior Art

Hose clamps of this type are already known. EP 0 995 461 A1, for example, thus describes a hose clamp which comprises an integral plastic body which extends in an elongate manner and has two arms connected to one another at the ends. At their inner sides, the two arms each form a projection such that the projections are disposed opposite one another in the closed state of the hose clamp and are dimensioned such that they pinch off the hose. Both arms can be hooked to one another in the closed state. The hose clamp has respective openings at its front and rear ends via which a hose, for example a catheter extension, can be received.

Such hose clamps are used, for example, on catheter extensions in the field of peritoneal dialysis. The clamp is located at the abdominal connector of the patient and serves the opening and closing of the catheter extension located at the abdominal connector. Since the clamp is in permanent contact with the skin of the patient, skin irritation frequently occurs due to the burrs and edges which are present with the already known clamp and with other commercially available clamps which are generally suitable for this use. The size and the shape are also perceived as irritating by the patient.

SUMMARY OF THE INVENTION

The object of the present invention comprises further developing the already named hose clamps such that they are no longer perceived as irritating in wear by the patient.

The object is solved in accordance with the invention by a hose clamp having the features described herein. Accordingly, the hose clamp generally has the shape of a cylinder with cut-off sides, with it tapering conically at both sides toward its ends and with the ends being adapted to the circular shape of a hose to be inserted. The idea of this new shape of the hose clamp comprises the fact that the basic form is derived from a cylinder and that the ends are configured to taper conically. To make possible a comfort in wear which is as large as possible, the shape of the hose clamp is adapted to the shape of the hose.

Advantageous aspects of the invention result from other features of the invention described herein. Accordingly, all edge regions of the hose clamp are rounded so that sharp edges and corners are avoided.

In accordance with a preferred embodiment, the length of the hose clamp does not exceed ten times the hose diameter. It is furthermore advantageous for the radii of the rounded plastic body to lie between R20 and R100. That is, the radius of the body, as designated by the value "R" in DIN (Deutsches Institut für Normung e.V.) 250, the standards for "Radii on workpieces and their representation in technical drawings," is a value that lies between R20 and R100.

It is furthermore advantageous for the plastic body to run out towards its ends at an angle of 5 degrees to 40 degrees to the longitudinal axis. A continuous transition from the hose to the clamp is hereby possible. In accordance with another preferred aspect, the outermost point of the hose clamp in the closed state is a maximum of twice the hose diameter away from the center of the hose to be inserted. A slim shape of the hose clamp is hereby defined which is no longer perceived as irritating by the patient.

For easier handling capability, gripping surfaces are cut out at the otherwise substantially cylindrical outer surface of the two arms.

The hooking mechanism is advantageously formed, on the one hand, by a projection facing toward the free end of the arm at the end of the hose clamp and, on the other hand, by a contact edge formed at the free end of the arm. In this context, a gripping surface is formed above the projection at the free end of the hose clamp via which the resilient end of the hose clamp can be deflected out of the latching position into a release position. It is hereby ensured that the hose clamp can be closed and opened a multiple of times.

BRIEF DESCRIPTION OF THE DRAWINGS

Further details and advantages of the invention result with reference to the embodiments shown in the enclosed drawings. There are shown:

FIG. 1: a side view of a hose clamp in accordance with the invention;

FIG. 2: the side view of FIG. 1 with a section line A-A drawn in;

FIG. 3: the section A-A of FIG. 2;

FIG. 4: a view from the front of a hose clamp of FIG. 1;

DETAILED DESCRIPTION OF THE PREFERRED EMBODIMENTS

Figure 5:
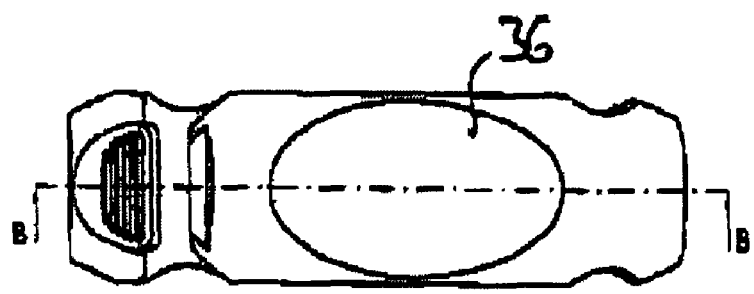
FIG. 5: a plan view from above of a hose clamp of FIG. 1.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

A hose clamp 10 in accordance with an embodiment of the present invention is shown in FIG. 1. The hose clamp 10 comprises an integral plastic body extending in an elongate manner and having two arms 12 and 14. The arms are connected to one another at an end 16 of the hose clamp, with them being shaped in the unloaded state such that the arm 14 is deflected by the angle $\alpha$ with respect to the arm 12. The arms 12 and 14 each have projections 18 and 20. A hose piece onto which the hose clamp is threaded can be closed by means of these projections. The arm 14 can be pivoted against the spring force of the end part 16 in the direction of the arm 12 and can be hooked with the end part 22 in the closed state. The hooking mechanism is formed, on the one hand, by a projection 24 facing the free end of the arm at the end part of the hose clamp 10 and, on the other hand, by a contact edge 26 formed at the free end of the arm. Respective mutually corresponding inclinations 28 and 30 are arranged at the front end of the contact edge 26 and at the corresponding end of the projection 24, said inclinations having the result that when the arm 14 is pressed down, the end 22 is deflected out so that the contact edge 26 comes to lie below the projection 24 so that hose clamp is hooked in the closed state.

A gripping surface 32 is additionally formed at the free end of the hose clamp and the resilient end 22 of the hose clamp can be deflected via it out of the latching position into a release position.

As can in particular be seen from FIG. 4, respective circular openings 34 are provided in the region of the front part 22, but also, as not shown in any more detail here, in the rear part 16 and the hose or catheter is introduced into the hose clamp through them.

The hose clamp 10 has a shape almost approximated to the shape of a cylinder with cut-off sides. The cylinder tapers conically toward both ends 16 and 22 and the respective ends 16 and 22 each have a circular shape which is adapted to that of the hose to be introduced. All edge regions in the hose clamp are rounded here as results, for example, from the sectional representation A-A of the arm 12 in accordance with FIG. 3.

Figure 6:
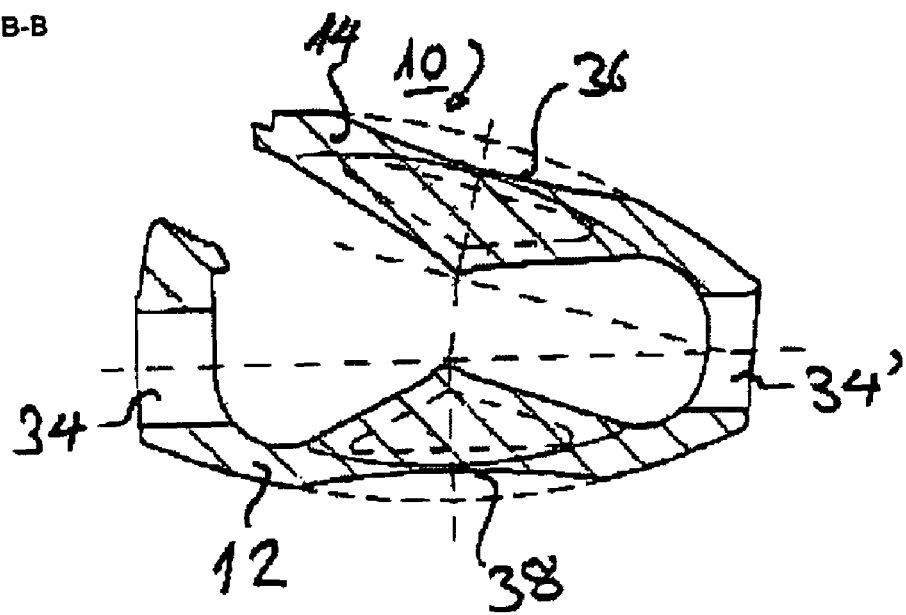
FIG. 6: a section B-B in accordance with FIG. 5.

As can in particular be seen from FIGS. 5 and 6, flattened portions are formed in each case at the periphery at the arms 12 and 14 as gripping surfaces 36 and 38 which permit a simpler handling capability.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A hose clamp comprising
an integral plastic body extending in an elongate manner and having two arms which are resiliently connected to one another at a first end of the body, and which each form a projection such that the arms are disposed opposite one another in a closed state of the hose clamp and are hooked with one another at a second end of the body in the closed state, with openings to receive a hose being provided at the first end and at the second end of the body,
the hose clamp being configured as a cylinder with cut-off sides which taper conically at both of the sides thereof toward the first and second ends, and the first and second ends being configured to accommodate a circular shape of the hose that is received therein.

2. The hose clamp in accordance with claim 1, further comprising rounded edge regions.

3. The hose clamp in accordance with claim 1, wherein a length of the hose clamp does not exceed 10 times a diameter of the hose.

4. The hose clamp in accordance with claim 1, wherein radii of the plastic body are between R20 and R100.

5. The hose clamp in accordance with claim 1, wherein the plastic body extends outward toward the first and second ends thereof at an angle of from 5° to 40° relative to a longitudinal axis of the plastic body.

6. The hose clamp in accordance with claim 1, wherein, when the hose clamp is in the closed state, an outermost point of the body lies at a maximum distance of twice a diameter of the hose away from a center of the hose that is received.

7. The hose clamp in accordance with claim 1, further comprising gripping surfaces provided at outer surfaces of both of the arms.

8. The hose clamp in accordance with claim 1, wherein the arms are hooked to one another by a mechanism provided at the second end of the body that includes (i) a projection on one of the arms and (ii) a contact edge on another of the arms.

9. The hose clamp in accordance with claim 8, further comprising a gripping surface provided on the arm above the projection to enable the arms to be deflected out of the hooked position into a release position.

10. The hose clamp according to claim 1, wherein the clamp is configured to close a catheter extension.

* * * * *

UNITED STATES PATENT AND TRADEMARK OFFICE
CERTIFICATE OF CORRECTION

PATENT NO. : 7,954,210 B2  
APPLICATION NO. : 11/883370  
DATED : June 7, 2011  
INVENTOR(S) : Andreas Ruffing It is certified that error appears in the above-identified patent and that said Letters Patent is hereby corrected as shown below:

Title Page, Item (57) Abstract, line 11, after "hose" insert -- that --.

Column 3, line 2, after "clamp" insert -- , --.

Column 3, line 3, after "deflected" insert -- , --; change "it" to -- the gripping surface 32, --; and after "position" insert -- and --.

Signed and Sealed this
Twenty-second Day of November, 2011

David J. Kappos
*Director of the United States Patent and Trademark Office*